US006575959B1

United States Patent
Sarge et al.

(10) Patent No.: US 6,575,959 B1
(45) Date of Patent: *Jun. 10, 2003

(54) CATHETER INCORPORATING AN INSERT MOLDED HUB AND METHOD OF MANUFACTURING

(75) Inventors: Jeffrey A. Sarge, Fremont, CA (US); Lex P. Jansen, Pleasanton, CA (US); Lawrence C. Alpert, Fremont, CA (US); Greg P Welsh, San Jose, CA (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/472,265

(22) Filed: Dec. 27, 1999

(51) Int. Cl.[7] .................. A61M 25/16; A61M 25/18; A61M 39/00; A61M 39/10

(52) U.S. Cl. ............... 604/533; 604/174; 128/DIG. 6; 128/DIG. 26

(58) Field of Search ..................... 604/93.01, 264, 604/523, 524, 533, 534, 539, 905, 535, 174, 177, 179, 180, 164.01–164.04, 164.06, 165.01; 128/DIG. 6, DIG. 26

(56) References Cited

U.S. PATENT DOCUMENTS

| | | | |
|---|---|---|---|
| 2,185,741 A | 1/1940 | Sorg et al. ................. 285/115 |
| RE25,788 E | 6/1965 | Sheridan ..................... 128/348 |
| 3,318,335 A | 5/1967 | Heller ......................... 285/114 |
| 3,348,544 A | 10/1967 | Braun ....................... 128/214.4 |
| 3,470,869 A | 10/1969 | Fenton et al. ................... 128/2 |
| 3,720,210 A * | 3/1973 | Diettrich .................. 128/214.4 |
| 3,725,522 A | 4/1973 | Sheridan et al. ............. 264/138 |
| 3,752,510 A | 8/1973 | Windischman et al. .. 285/334.4 |
| 3,861,972 A | 1/1975 | Glover et al. .................. 156/86 |
| 3,865,666 A | 2/1975 | Shoney ........................ 156/245 |
| 3,873,391 A | 3/1975 | Plauka et al. ................ 156/258 |
| 3,914,002 A | 10/1975 | Berliner et al. ................ 339/16 |
| 3,950,052 A | 4/1976 | Walter et al. ................ 339/101 |
| 3,959,429 A | 5/1976 | Benning ..................... 264/155 |
| 3,985,601 A | 10/1976 | Panagrossi .................. 156/229 |
| 3,989,571 A | 11/1976 | Harautuneian ............... 156/250 |
| 4,085,185 A | 4/1978 | Adair ......................... 264/248 |
| 4,093,484 A | 6/1978 | Harrison et al. ........ 156/244.13 |
| 4,154,244 A | 5/1979 | Becker et al. .............. 128/349 |
| 4,171,943 A | 10/1979 | Tschanz et al. ............. 425/392 |

(List continued on next page.)

FOREIGN PATENT DOCUMENTS

| EP | 0 437 291 B1 | 12/1993 |
| GB | 2 187 670 A | 9/1987 |

*Primary Examiner*—Brian L. Casler
*Assistant Examiner*—Jennifer Maynard
(74) *Attorney, Agent, or Firm*—Crompton, Leager & Tufte, LLC

(57) ABSTRACT

A catheter for use in vasculature or other lumens within body structures includes a shaft formed from an elongated polymeric flexible tube. A thin polymeric sleeve is placed over a proximal portion of the catheter shaft. A hub structure is injection molded over the sleeve with a polymer of the same type as the polymeric sleeve. The heat from the injection molded polymer of the hub body is sufficient to heat the polymeric sleeve, causing the polymeric sleeve to bond the hub body to the sleeve, and the sleeve to the catheter shaft. In this way, the injection molded polymeric hub structure is fused to the catheter shaft, with a unified polymeric bond, and without the use of adhesive. The plastic sleeve is sufficiently thick to protect the catheter shaft from the heat of the injection molded molten polymer while still allowing the catheter shaft and sleeve to bond to the shaft.

11 Claims, 3 Drawing Sheets

U.S. PATENT DOCUMENTS

| | | | |
|---|---|---|---|
| 4,191,185 A | 3/1980 | Lemieux | 128/214.4 |
| 4,198,983 A | 4/1980 | Becker et al. | 128/349 |
| 4,207,900 A | 6/1980 | Patel et al. | 128/349 B |
| 4,210,478 A | 7/1980 | Shoney | 156/242 |
| 4,284,459 A | 8/1981 | Patel et al. | 156/245 |
| 4,328,056 A | 5/1982 | Snooks | 156/242 |
| 4,354,495 A | 10/1982 | Bodicky | 128/348 |
| 4,489,961 A | 12/1984 | Laidig | 285/116 |
| 4,509,877 A | 4/1985 | Sobin et al. | 285/114 |
| 4,511,163 A | 4/1985 | Harris et al. | 285/177 |
| 4,531,943 A | 7/1985 | Van Tassel et al. | 604/280 |
| 4,557,781 A | 12/1985 | Hoppie | 156/245 |
| 4,592,749 A * | 6/1986 | Ebling et al. | 604/283 |
| 4,596,563 A | 6/1986 | Pande | 604/264 |
| 4,602,808 A | 7/1986 | Herron et al. | 285/115 |
| 4,655,762 A | 4/1987 | Rogers | 604/905 |
| 4,737,219 A | 4/1988 | Taller et al. | 156/215 |
| 4,753,765 A | 6/1988 | Pande | 264/149 |
| 4,778,550 A | 10/1988 | Barton et al. | 156/211 |
| 4,802,947 A * | 2/1989 | Bartholomew | 156/380.5 |
| 4,806,182 A | 2/1989 | Rydell et al. | 156/211 |
| 4,826,480 A | 5/1989 | Diaz et al. | 604/280 |
| 4,838,269 A * | 6/1989 | Robinson et al. | 128/344 |
| 4,842,590 A | 6/1989 | Tanabe et al. | 604/282 |
| 4,863,441 A | 9/1989 | Lindsay et al. | 604/280 |
| 4,863,442 A | 9/1989 | DeMello et al. | 604/282 |
| 4,874,373 A | 10/1989 | Luther et al. | 604/164 |
| 4,875,481 A * | 10/1989 | Higgins | 128/344 |
| 4,886,506 A | 12/1989 | Lovgren et al. | 604/280 |
| 4,950,257 A | 8/1990 | Hibbs et al. | 604/265 |
| 4,959,067 A | 9/1990 | Muller | 606/190 |
| 4,960,412 A | 10/1990 | Fink | 604/167 |
| 5,035,686 A | 7/1991 | Crittenden et al. | 604/96 |
| 5,041,095 A | 8/1991 | Littrell | 604/167 |
| 5,085,645 A | 2/1992 | Purdy et al. | 604/167 |
| 5,125,903 A | 6/1992 | McLaughlin et al. | 604/167 |
| 5,125,913 A | 6/1992 | Quackenbush | 604/264 |
| 5,129,887 A | 7/1992 | Euteneuer et al. | 606/194 |
| 5,139,032 A * | 8/1992 | Jahrmarkt et al. | 128/772 |
| 5,143,409 A | 9/1992 | Lalikos | 285/116 |
| 5,160,559 A | 11/1992 | Scovil et al. | 156/73.6 |
| 5,167,647 A * | 12/1992 | Wijkamp et al. | 604/281 |
| 5,181,750 A | 1/1993 | Reum | 285/115 |
| 5,190,529 A | 3/1993 | McCrory et al. | 604/175 |
| 5,201,723 A | 4/1993 | Quinn | 604/264 |
| 5,217,555 A | 6/1993 | Franklin, III et al. | 156/156 |
| 5,221,270 A | 6/1993 | Parker | 604/282 |
| 5,226,898 A | 7/1993 | Gross | 604/243 |
| 5,240,537 A | 8/1993 | Bodicky | 156/244.13 |
| 5,248,305 A | 9/1993 | Zdrahala | 604/280 |
| 5,254,107 A | 10/1993 | Soltesz | 604/282 |
| 5,279,596 A | 1/1994 | Castaneda et al. | 604/282 |
| 5,300,032 A | 4/1994 | Hibbs et al. | 604/164 |
| 5,312,356 A | 5/1994 | Engelson et al. | 604/164 |
| 5,318,032 A | 6/1994 | Lonsbury et al. | 128/658 |
| 5,330,444 A | 7/1994 | Webler et al. | 604/265 |
| 5,330,449 A | 7/1994 | Prichard et al. | 604/282 |
| 5,358,493 A * | 10/1994 | Schweich, Jr. et al. | 604/264 |
| 5,376,077 A | 12/1994 | Gomringer | 604/167 |
| 5,380,301 A * | 1/1995 | Prichard et al. | 604/281 |
| 5,395,332 A | 3/1995 | Ressemann et al. | 604/96 |
| 5,403,292 A | 4/1995 | Ju | 604/264 |
| 5,466,230 A | 11/1995 | Davila | 604/256 |
| 5,507,728 A | 4/1996 | Erskine | 604/164 |
| 5,533,988 A | 7/1996 | Dickerson et al. | 604/282 |
| 5,545,151 A | 8/1996 | O'Connor et al. | 604/282 |
| 5,558,635 A | 9/1996 | Cannon | 604/164 |
| 5,558,652 A | 9/1996 | Henke | 604/256 |
| 5,569,218 A | 10/1996 | Berg | 604/280 |
| 5,695,467 A | 12/1997 | Miyata et al. | 604/280 |
| 5,762,637 A | 6/1998 | Berg et al. | 604/264 |
| 5,772,642 A | 6/1998 | Ciamacco, Jr. et al. | |
| 5,803,510 A | 9/1998 | Dorsey, III | 604/283 |
| 5,830,401 A | 11/1998 | Prichard et al. | 264/262 |
| 6,033,388 A * | 3/2000 | Nordstrom et al. | 604/264 |
| 6,074,379 A | 6/2000 | Prichard | |
| 6,228,073 B1 | 5/2001 | Noone et al. | |
| 6,273,404 B1 | 8/2001 | Holman et al. | |
| 6,332,874 B1 * | 12/2001 | Eliasen et al. | 604/174 |

\* cited by examiner

CATHETER INCORPORATING AN INSERT MOLDED HUB AND METHOD OF MANUFACTURING

FIELD OF THE INVENTION

The present invention relates to guide, diagnostic, and therapeutic catheters for use in medical procedures. In particular, the present invention relates to an improved therapeutic micro-catheter proximal hub and method of manufacture, wherein the hub is molded around the catheter shaft over a shielding sleeve which prevents damage to the catheter shaft while assuring adequate bonding of the hub to the shaft.

BACKGROUND OF THE INVENTION

The present invention relates to the field of catheterization of lumens within the human body, particularly lumens in the cerebral, peripheral, and heart vasculature. The invention has application to the manufacture and construction of guide, diagnostic, and drug delivery catheters, as well as balloon catheters.

Many medical procedures include the insertion of a catheter into a lumen of a living body. In the performance of such medical procedures, guide catheters and diagnostic catheters are well known for use in catheterization procedures in the vascular system, such as angiography, angioplasty, and other diagnostic or interventional procedures, such as interventional radiology.

One useful therapeutic application of intravascular catheters is the treatment of intracranial aneurysms in the brain. Approximately 25,000 intracranial aneurysms rupture each year in North America. An aneurysm which is likely to rupture, or one which has already ruptured, may be treated by delivering an embolic device or agent to the interior of the aneurysm. The embolic device or agent encourages the formation of a thrombus inside the aneurysm. The formation of a thrombus reduces the probability that an aneurysm will rupture. The formation of a thrombus also reduces the probability that a previously ruptured aneurysm will re-bleed. Thrombus agents which may be used include liquid thrombus agents such as cyanocrylate, and granulated thrombus agents such as polyvinyl alcohol or alcohol. An additional type of thrombus agent which is frequently used is a tiny coil. Any of the thrombus agents described above may be delivered using an intravascular catheter.

When treating an aneurysm with the aid of an intravascular catheter, the catheter tip is typically positioned proximate the aneurysm site. The thrombus agent is then urged through the lumen of the intravascular catheter and introduced into the aneurysm. Shortly after the thrombus agent is placed in the aneurysm, a thrombus forms in the aneurysm and is shortly thereafter complemented with a collagenous material which significantly lessens the potential for aneurysm rupture. It is desirable that the lumen of the catheter provides a path for delivering embolic devices to an aneurysm. To this end, it is desirable that the pathway through the catheter have a low friction surface.

In other portions of the human body, diagnostic catheters are used for procedures including dye delivery, arterial flushing or arterial pressure monitoring. Diagnostic catheters are also used during cardiac catheterization for diagnosis of coronary artery disease, for defining vessel anatomy, for isolating lesions, and for identifying adjacent cardiac branches which may impinge on a lesion and affect ventricular function. For procedures within the coronary artery, the distal end of the diagnostic catheter is inserted percutaneously into the vascular system of the patient and pushed distally up and over the aortic arch. A proximal end of the catheter protrudes outside of the patient's body and may be used for implementation of diagnostic procedures, such as dye delivery, flushing, and arterial pressure monitoring.

Angioplasty procedures have gained wide acceptance as an efficient and effective method for treating certain types of vascular diseases. In particular, angioplasty is widely used for stenoses in the coronary arteries, although it is also used for the treatment of stenoses in other parts of the vascular system. The most widely used form of angioplasty makes use of a dilatation balloon catheter to treat a stenosis and thereby reestablish an acceptable blood flow through the artery. The dilatation catheter includes an elongated tubular shaft and an inflatable balloon carried at a distal end of the shaft. In operation, the catheter is inserted through a guide catheter which has been previously introduced into a patient's vascular system from a location remote from the heart (e.g., femoral artery). The proximal end of the guide catheter remains outside the patient while the distal end of the guide catheter is positioned at the coronary artery ostium. A dilatation catheter is introduced into the proximal end of the guiding catheter and advanced to the distal end of the guide catheter. Then, by using fluoroscopy, the physician guides the dilatation catheter the remaining distance through the vascular system until the balloon is positioned across the stenosis.

In each of the above applications, the catheter commonly includes a hub and/or manifold at its proximal end, which permits the catheter to be more easily handled, and which may incorporate a luer fitting or other connection device which may be attached to an appliance conveying a fluid media or substance which is to be delivered to the distal end of the catheter. In some known catheters, hubs are adhesively bonded to the catheter shaft, while in other known designs, hubs are injection or insert molded onto the catheter shafts. With the insert molding process, the injected molten plastic hub material, because of its high temperature, may be capable of damaging the shaft of the catheter by melting or otherwise deforming it. This may compromise the integrity of the lumen walls in the affected region which may lead to collapse by kinking or other deformation that reduces the lumen diameter.

Under prior methods of injection or insert molding hubs onto catheter shafts, the catheter shaft was afforded protection from the high temperatures of the injected hub material by protective layers placed over the catheter shafts. For example, the catheter shaft might be protected by multiple layers of polymeric films over the catheter shaft in the region of hub attachment. In order to ensure good adhesion of the catheter hub to the shaft, these multiple protective layers require separate lamination of each layer to the shaft and to each other. Accordingly, these prior methods of securing hubs to catheter shafts had a number of drawbacks. The preparation of the catheter shaft prior to hub molding increased the complexity of catheter manufacture, and the increased preparatory steps afforded increased chances for error, quality variations, and rejected products and waste, in addition to increased time and cost of manufacture.

It is desirable to have a plastic molded hub, and a manufacturing process for these hubs, which is less labor intensive than prior methods of producing such catheters with hubs, and which would have reduced defect and scrap rates relative to present techniques of securing the hub to the catheter shaft.

SUMMARY OF THE INVENTION

The present invention pertains to a process for the production of intralumenal catheters with an insert molded hub, that does not require extensive preparation of the catheter shaft prior to molding. One embodiment of the present invention provides for a tubular sleeve of material that is compatible with the hub molding media. The tubular sleeve shields the catheter shaft from heat generated during the injection molding process, but transfers enough heat for bonding the sleeve to the catheter shaft. The compatible material of the tubular sleeve thermally bonds with the shaft on the sleeve's inner diameter, and bonds with the hub molding media on the sleeve's outer diameter during the single injection molding step. The present invention overcomes disadvantages of previously existing methods for securing the hub to the catheter shaft, and accomplishes hub molding with fewer errors in manufacture. The present invention therefore increases the reliability of the production process, in addition to making the hub to catheter shaft transition seamless, i.e., without weld lines, and therefore more securely affixed to the catheter shaft and less prone to failure or bursting. In addition, fewer additional materials are introduced into production of the catheter.

One embodiment of the present invention is a catheter with a flexible, elongate tubular shaft. This shaft has a lumen therethrough, and has a proximal and a distal end. The catheter shaft may be of any length required to reach the site of therapeutic or diagnostic activity within the patient vasculature, and may also incorporate various therapeutic or diagnostic devices or means at the distal end of the catheter shaft, including an expandable balloon, for example. A hub with an inner lumen is attached to the proximal end of the shaft. A thin polymeric sleeve covers the proximal end of the catheter shaft, and may extend slightly beyond the proximal end of the catheter shaft.

This polymeric sleeve is preferably heat fused to the catheter shaft, and is covered over most of its length by the molded hub of the catheter. Generally, the tubular sleeve must extend over any part of the catheter shaft that will be contacted by the hot melt injection during hub molding.

In a preferred embodiment, the hub injectate material is a polymer such as polyamide, nylon, polyether block amide (PEBA), or mixtures and copolymers thereof. A preferred commercially available suitable material is Grilamid® TR55LX produced by EMS-Chemie Holding AG/American Grilon, Inc. of Sumter, S.C. Also in a preferred embodiment, the protective sleeve placed over the catheter shaft is made from the identical material. Generally, however, any compatible material for the sleeve will support the subject invention. By a compatible material, it is meant that the sleeve material will form a thermal bond to the shaft, and will also bond to the hot injectate during the molding process. In preferred embodiments, the injectate provides sufficient heat to form the sleeve bond to the shaft by conduction therethrough. Further, in preferred embodiments, the sleeve and injectate material are both clear or optically clear to form a unitary clear hub.

Under a preferred embodiment of the subject invention utilizing a Grilamid® polymeric sleeve and injectate, where the catheter shaft is made with an inner layer of a fluoropolymer or thermoplastic, and an outer layer of a thermoplastic such as a polyether block amide (PEBA), the polymeric sleeve will have a wall thickness within a range of approximately 0.005 inches to 0.020 inches, while the injectate hub hot media will be heated and injected at a temperature of approximately 450° F. to 550° F. Following the injection, the hot media is preferably cooled by conduction via a recirculating coolant. Regardless of the polymeric material used to practice or produce the subject invention, the parameters must be regulated so as to ensure an effective heat bond between the inner diameter of the polymeric sleeve and the outer wall of the catheter shaft, but without permitting excessive heat to be conveyed to the catheter shaft so as to permit damage to the shaft.

Another embodiment of the present invention incorporates a flexible strain relief sheathing, surrounding the catheter shaft distal to the area of the hub, but in close proximity to the hub, to prevent crimping and to help prevent a degree of bending that may damage the shaft in the area where it meets the hub. The strain relief is flexible, but not as flexible as the shaft in the area distal to the hub. In a preferred embodiment, the flexible strain relief becomes more difficult to flex as it is flexed, and becomes very difficult to flex as it approaches a degree of flexion wherein the shaft surrounded by the strain relief is near its limit of flexion, i.e., at a point where it is in danger of kinking or folding.

In preferred embodiments, the flexible strain relief is added to the hub after molding and curing of the hub is complete. The strain relief may be made from a polymeric material different than that from which the hub is made. In an alternative embodiment of the present invention, an integral strain relief that is molded as part of, or as an extension of, the hub itself may be utilized. An integrated hub and strain relief is disclosed in commonly assigned pending U.S. patent application Ser. No. 08/971,456, filed Nov. 17, 1997, entitled "Integral Hub and Strain Relief," the disclosure of which is hereby incorporated by reference.

In this embodiment of the subject invention, the polymeric sleeve placed around the catheter shaft will naturally be longer, because the material that is to adhere to the catheter shaft, i.e., the hub and strain relief integrated structure, is longer than the hub structure alone. Because the strain relief, when injection molded, will be at a temperature that may damage the catheter shaft, the polymeric sleeve must be extended to protect the catheter shaft from this additional molded member. When the strain relief member is integrated with the hub, the polymeric sleeve is used to adhere the integral molded hub and strain relief structure to the catheter shaft, in the same way that the sleeve is used to bond the hub to the shaft in the embodiments of the invention previously discussed.

The present invention further includes a method for manufacturing the hub, and the attendant attachment of the sleeve and hub to the catheter shaft. With this method, the proximal end of the catheter shaft is placed over a pin in a molding core. Thereafter, a polymeric tubular sleeve is placed over the catheter shaft, and is slid down the catheter shaft to the proximal end. In a preferred embodiment, the polymeric sleeve may extend just beyond the proximal tip of the catheter shaft, or may be flush with the proximal tip. Similarly, the distal end of the polymeric sleeve may be flush with the distal end of the catheter hub as defined by the mold, or, in a preferred embodiment, may extend slightly distally of the distal end of the catheter hub. Thereafter, the polymeric material of the catheter hub is injected into the molding core or cavity in which the catheter shaft has been placed. In a preferred embodiment of the subject invention, the heat of the molten hub material imparts sufficient heat to the polymeric sleeve to fuse the polymeric sleeve to the catheter shaft, and to fuse the polymeric sleeve with the hub itself into one unified member; however, the polymeric sleeve is sufficiently thick so that the heat from the molten hub material does not melt or otherwise deform or damage the catheter shaft.

BRIEF DESCRIPTION OF THE DRAWINGS

The invention will be further described with reference to the accompanying drawings.

DETAILED DESCRIPTION OF THE INVENTION

Figure 1:
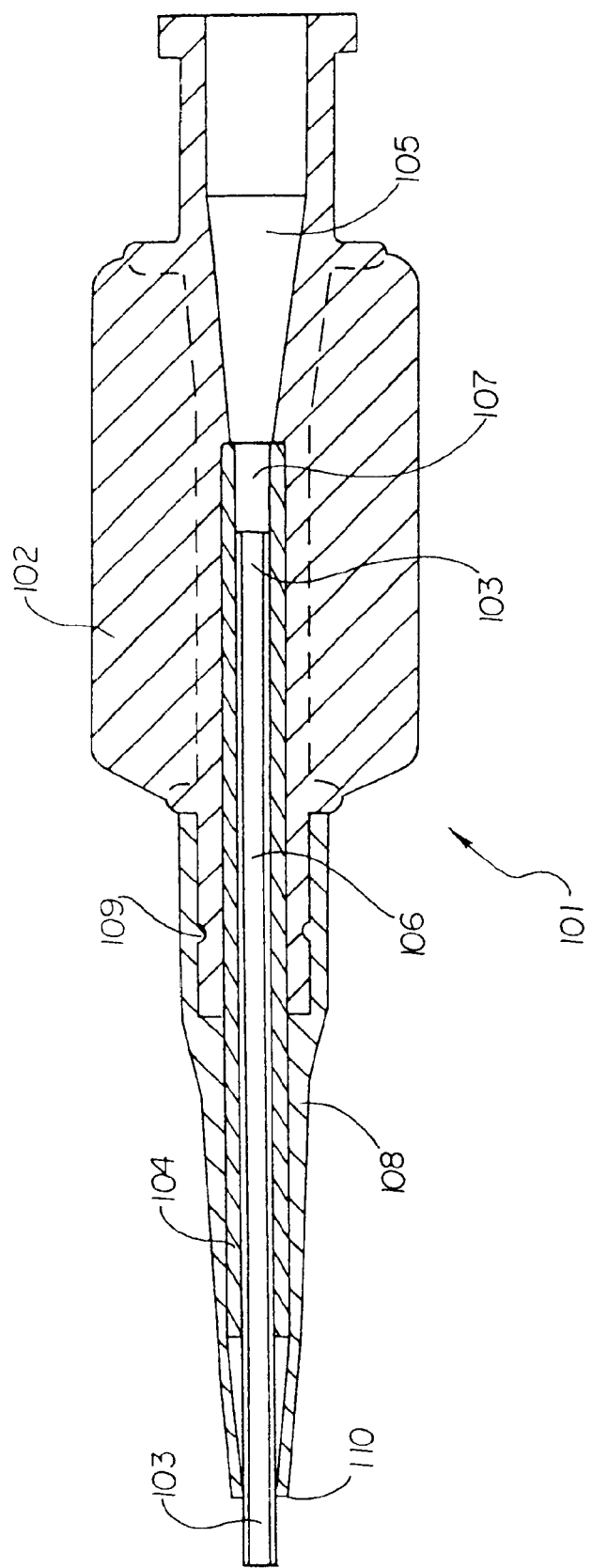
FIG. 1 is a cross-sectional view of the hub of a catheter of the present invention.

FIG. 1 depicts a proximal portion of a catheter 101 of the subject invention, showing the hub 102, the catheter shaft 103, and the polymeric sleeve 104. In FIG. 1, the polymeric sleeve 104 is shown as a distinct separate member. Insert molding of the hub 102 over the sleeve will, however, reduce or eliminate the distinctiveness of this element, especially when the same polymer is used for the sleeve 104 and hub 102. FIG. 1 shows the separate elements so that the function of the sleeve 104 as a heat shield for the shaft may be better understood. The hub lumen 105 is in fluid communication with the catheter shaft lumen 106, with an intermediate lumen 107 of the polymeric sleeve, if the polymeric sleeve extends past the proximal end of the catheter shaft 103, as is depicted. The distal end of the catheter shaft is not depicted, but may be an infusion catheter, a balloon angioplasty catheter, or other diagnostic or therapeutic catheter. A strain relief member 108 is used to prevent kinking and bending of catheter shaft 103. This strain relief may be press fit onto the catheter hub after molding, and is held in place by the radial depression in the hub 109. In an alternate embodiment of the present invention, the strain relief member 108 may be integrated with the catheter hub 102 to form an integrated hub and strain relief member. In this instance, the polymeric sleeve 104 would preferably extend to a further distal point at least to the distal end 110 of the strain relief member 108.

Figure 2:
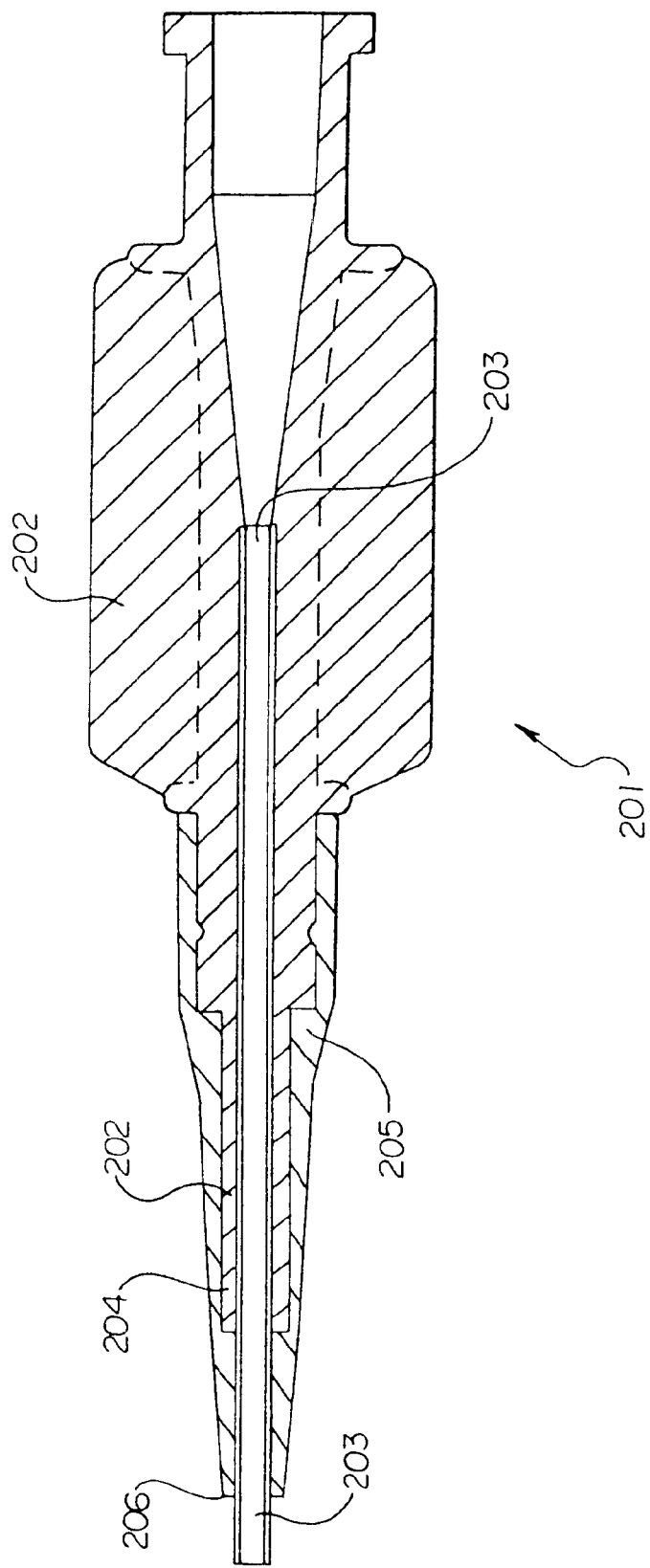
FIG. 2 is a plan view of the proximal (hub) portion of the catheter of FIG. 1 following manufacture according to the subject invention.

FIG. 2 is a detailed view of the catheter hub 102 of FIG. 1, showing the fusion of the catheter hub and polymeric sleeve resulting from injection molding of the catheter hub 102. FIG. 2 shows generally a hub assembly 201 according to one embodiment of the subject invention. While the subject invention is depicted in FIG. 1 with the polymeric sleeve 102 and the catheter hub 104 as separate structures, after the molding process, a preferred embodiment results in a fusion of the two structures into a single unified structure 202, fused to the catheter shaft 203. In a preferred embodiment, the fusion or unification of the two structures, the polymeric sleeve 102 and the catheter hub 104 is so complete so as to have no discernable seam or weld line. Therefore, while as depicted in FIG. 1, the polymeric sleeve 104 is separate and distinct from the catheter hub 102, in the finished article, these would appear as a single structure made from a uniform material. In other words, in FIG. 1, the polymeric sleeve 104 was separate from the catheter hub 102, as might be seen for an instant following injection of the molten hub material. However, the polymeric sleeve 104 in FIG. 1 will quickly fuse to the catheter hub 102, to form an integrated hub and sleeve structure 202. Because the polymeric sleeve 104 surrounds the catheter shaft 103, and may extend distally of the distal end of the catheter hub 102, an artifact of the sleeve 104 is seen as the distal extension 204 of the integrated hub and sleeve structure 202.

A flexible strain relief member 205 may be placed over the hub 204, to form a transitional flexibility between the relatively rigid hub 202 and the relatively flexible unsupported catheter shaft 203. This flexible strain relief 205 may be press fit onto the catheter hub and held in place by a ridge 206 which radially encircles the hub 205. In an alternate embodiment, the flexible strain relief 205 may be formed as an integral structure with the hub 202. In this embodiment, the polymeric sleeve, seen in FIG. 2 as hub extension 204, is preferably lengthened to extend to a point at least as distal as the distal end 206 of the strain relief member 205.

Figure 3:
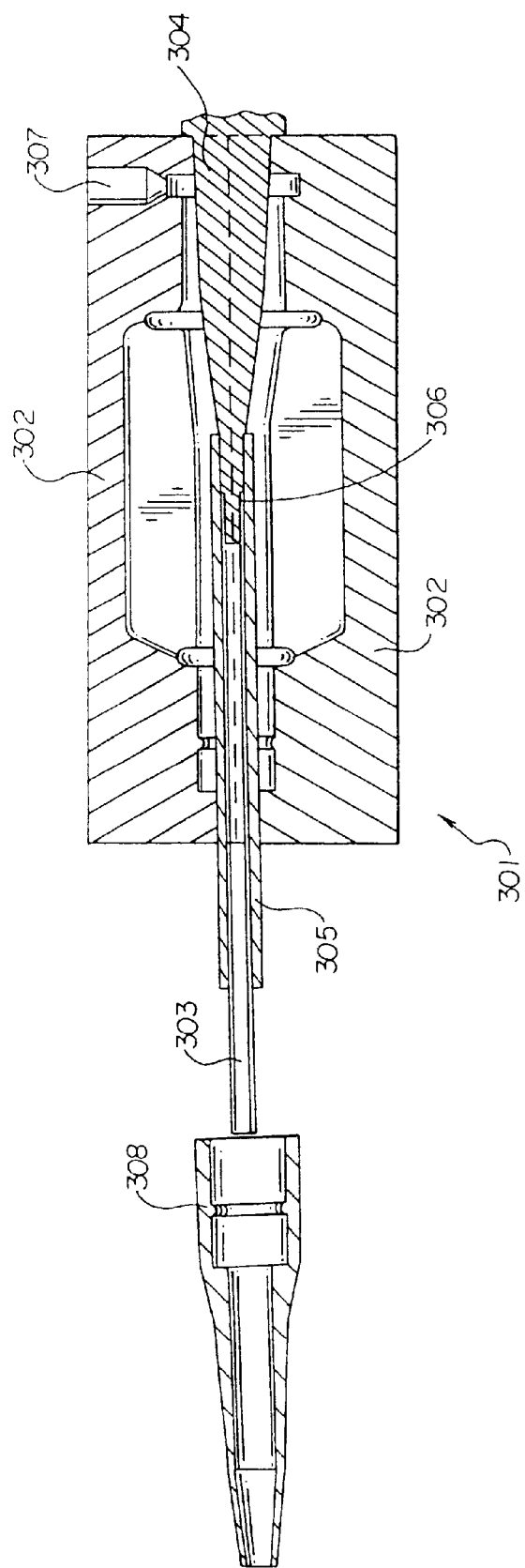
FIG. 3 is a cross section of an apparatus used to manufacture the catheter of the subject invention.

FIG. 3 depicts an injection molding apparatus suitable for use in one embodiment of the subject invention disclosing a method of producing catheters with molded hubs unified with a polymeric sleeve, which is fused to a catheter shaft. The injection molding device, with a catheter shaft 303 and sleeve assembly 305 inserted therein, is depicted generally at 301. The mold is depicted at 302, while the catheter shaft 303 of the catheter being produced by the subject method is depicted at 303. The catheter being produced is disposed with its lumen over a holding pin or mandrel 304. Onto the catheter shaft 303 and prior to molding, a polymeric protective sleeve 305 is slid down around the catheter shaft 303, down to the proximal end 306 of the catheter shaft 303, proximate to the molding pin 304. The polymeric sleeve may extend proximally to the proximal end 306 of catheter shaft 303, as depicted.

A suitable polymeric molten or otherwise liquid or uncured polymeric substance is injected into the injection mold 302, through injection port 307. After the polymeric material has cooled, if previously molten, or otherwise cured, the catheter shaft 303 may be removed from the holding pin 304. The resulting catheter hub formed by injection mold 302 is adhered or fused to polymeric sleeve 305 to form a combined unified structure similar to that depicted in FIG. 2. The heat of the molten polymeric material, or other aspect of the polymeric material that keeps the molding media liquid or uncured, also serves to make the polymeric sleeve 305 adhere or bond to the catheter shaft 303 by heat bonding of sleeve 305 to the shaft, or by otherwise bringing the polymeric sleeve to an uncured state in which bonding with the catheter shaft 303 is effected. In the instance of using melted polymeric material as the injectate, the temperature of the molten polymeric material being injected into the molding chamber should be between approximately 450° F. and 550° F. In addition to effecting bonding of the polymeric sleeve 305 to the catheter shaft 303, the melting or uncuring of the polymeric sleeve 305 should effect bonding between the hub structure and the polymeric sleeve to the extent that they form a unified assembly, as discussed previously. Both the hub structure material and sleeve material are preferably clear or optically clear. Separate strain relief member 308 is depicted in FIG. 3, and may be press fit onto the hub formed by mold 302.

The present invention may be used to manufacture any catheter including a shaft and hub assembly indisposed on the proximal end thereof. The shafts can include monolithic polymeric shafts or multi-layer shafts which may or may not incorporate a braided reinforcement structure. The present invention is particularly useful when used in conjunction with catheter shafts having relatively small diameters and thin tube walls. These features are preferred in catheters which are utilized to reach small vessel lumens because the lumen diameter is optimized to be as large as possible throughout the length of the catheter. As such, the thin wall of the shaft is more susceptible to damage from the molten material during the injection molding process. It is believed that the present invention can be utilized with any combination of polymeric materials which lead to a satisfactory bond strength between the hub, the sleeve, and the outside surface of the catheter shaft. In preferred embodiments, the sleeve and hub material are the same.

Applicants recognize that the thickness of the tube wall of the sleeve must be selected in conjunction with several parameters in order for adequate bonds to be formed in the process of the present invention. In particular, the sleeve thickness must be selected in combination with selecting the temperature of the molten injection material so that there is sufficient heat to cause the inside diameter of the sleeve to bond to the outside diameter of the shaft. At the same time, the sleeve must be thick enough to prevent too much heat to be conducted from the molten polymer to the shaft so that there is damage to the shaft, itself. Experimentation with operating conditions is believed required for each catheter design. In a preferred embodiment, the shaft sleeve has a wall thickness of about 0.0005 inches to about 0.020 inches, and the injectate has a temperature of about 450° F. to about 550° F. When these parameters are selected in conjunction with a preferred Grilamid® sleeve and hub material, adequate bonds are formed while preventing any damage to the catheter shaft.

Although the preceding description of the invention is directed to an infusion catheter, it will be appreciated by those skilled in the art that the invention may be used on other interventional catheters with lumenal or vascular interoperative devices having a hub or manifold, such as atherectomy devices, ultrasonic imaging and therapeutic catheters, laser catheters, stent delivery catheters, and perfusion catheters.

Although the present invention has been described with reference to preferred embodiments, workers skilled in the art will recognize that changes may be made in form and detail without departing from the spirit and scope of the invention.

What is claimed is:

1. A catheter assembly comprising:

an elongate flexible tubular shaft having a proximal end and a distal end, with a radial wall defining a lumen extending longitudinally between the proximal end and the distal end;

a polymeric tubular sleeve placed onto the tubular shaft so as to cover at least a proximal portion of the outer surface of the radial wall of the tubular shaft, said polymeric tubular sleeve having a proximal end extending proximally beyond the proximal end of the tubular shaft and a distal end, with a radial wall defining a lumen extending longitudinally between the proximal end and the distal end, said sleeve being open at the distal and proximal ends, the sleeve being fused to the tubular shaft; and a hub of a polymeric material molded over and fused to the polymeric sleeve at the proximal end of the tubular shaft, said hub defining a lumen therein, the hub lumen having an inner wall, said hub being disposed around the tubular shaft and covering at least part of the polymeric sleeve such that the distal end of the polymeric sleeve extends distally of the hub.

2. A catheter assembly as defined in claim 1, wherein the polymeric sleeve covers only a proximal portion of the outer surface of the radial wall of the tubular shaft.

3. A catheter assembly as defined in claim 1, wherein the polymeric hub is injection molded onto the proximal portion of the tubular shaft, over the polymeric sleeve.

4. A catheter assembly as defined in claim 1, wherein the molded hub and the polymeric sleeve are made from the same polymeric material.

5. A catheter assembly as defined in claim 4, wherein both said polymeric sleeve and said hub material are clear.

6. A catheter assembly as defined in claim 4, wherein said polymeric sleeve is fused by heat to the tubular shaft in at least a proximal portion.

7. A catheter assembly as defined in claim 3, wherein the material from which the hub is made is heated to a temperature between 450° F. and 550° F. prior to being injected into a hub mold.

8. A catheter assembly as defined in claim 7, wherein the molded hub and the polymeric sleeve are manufactured from a material selected from the group consisting of nylon, polyamide, polyether block amide, and mixtures or copolymers thereof.

9. A catheter assembly as defined in claim 1, wherein said polymeric sleeve and said hub have been fused together into a unified structure.

10. A catheter assembly as defined in claim 1, wherein the polymeric sleeve has a radial wall thickness of approximately 0.005 inches to 0.020 inches.

11. A catheter assembly as defined in claim 1, wherein a flexible strain relief member is disposed over a distal section of the molded hub, and surrounds the shaft proximate and distal to said hub.

* * * * *

UNITED STATES PATENT AND TRADEMARK OFFICE
CERTIFICATE OF CORRECTION

PATENT NO. : 6,575,959 B1
DATED : June 10, 2003
INVENTOR(S) : Jeffrey A. Sarge et al.

It is certified that error appears in the above-identified patent and that said Letters Patent is hereby corrected as shown below:

Title page,
Item [54], Title, delete "MANUFACTURING", and insert therefor
-- MANUFACTURE --.

Item [74], *Attorney, Agent, or Firm*, delete "Leager" and insert therefor -- Seager --.

Signed and Sealed this

Seventh Day of October, 2003

JAMES E. ROGAN
*Director of the United States Patent and Trademark Office*